US011001893B2

(12) United States Patent
Roses (10) Patent No.: US 11,001,893 B2
(45) Date of Patent: May 11, 2021

(54) METHODS FOR DETECTING STRUCTURAL VARIANTS IN NEURODEGENERATIVE DISEASE (71) Applicants: Zinfandel Pharmaceuticals, Inc., Chapel Hill, NC (US); Ann M. Saunders

(72) Inventor: Allen D. Roses, Chapel Hill, NC (US)

(73) Assignee: ZINFANDEL PHARMACEUTICALS, INC., Chapel Hill, NC (US)

( * ) Notice: Subject to any disclaimer, the term of this patent is extended or adjusted under 35 U.S.C. 154(b) by 0 days.

(21) Appl. No.: 16/308,315

(22) PCT Filed: Jun. 9, 2017

(86) PCT No.: PCT/US2017/036682
§ 371 (c)(1),
(2) Date: Dec. 7, 2018

(87) PCT Pub. No.: WO2017/214471
PCT Pub. Date: Dec. 14, 2017

(65) Prior Publication Data
US 2019/0256914 A1 Aug. 22, 2019

Related U.S. Application Data (60) Provisional application No. 62/348,287, filed on Jun. 10, 2016.

(51) Int. Cl.
C12Q 1/68 (2018.01)
C12P 19/34 (2006.01)
C12Q 1/6883 (2018.01)

(52) U.S. Cl.
CPC ............ *C12Q 1/6883* (2013.01); *C12Q 1/68* (2013.01); *C12Q 2600/106* (2013.01); *C12Q 2600/112* (2013.01); *C12Q 2600/156* (2013.01)

(58) Field of Classification Search
CPC ... C12Q 1/68; C12Q 1/6883; C12Q 2600/156
See application file for complete search history.

(56) References Cited

U.S. PATENT DOCUMENTS

| 2002/0062493 | A1 | 5/2002 | Eggan et al. |
| 2010/0028931 | A1 | 2/2010 | Eggan et al. |
| 2014/0322237 | A1 | 10/2014 | Eggan et al. |
| 2014/0348822 | A1 | 11/2014 | Cashman et al. |
| 2015/0190363 | A1 | 7/2015 | Woolf et al. |
| 2015/0301058 | A1 | 10/2015 | Schettini et al. |
| 2016/0068904 | A1 | 3/2016 | Harper |

FOREIGN PATENT DOCUMENTS

| WO | 2013/030588 | 3/2013 |
| WO | 2013/041577 | 3/2013 |
| WO | 2013/055865 | 4/2013 |
| WO | 2015/089333 | 6/2015 |
| WO | 2015/143078 | 9/2015 |

OTHER PUBLICATIONS

DbSNP Submitted SBP(ss) Report in Submission Format for NCBI Assay Id(ss#): ss1712236748, Mar. 4, 2015, 1 printed page from https://www.ncbi.nlm.nih.gov/projects/SNP/snp (Year: 2015).*
DbSNP Submitted SNP(ss) Report in Submission Format for NCBI Assay Id(ss#): ss1712236749, Mar. 4, 2015, 1 printed page from https://www.ncbi.nlm.nih.gov/projects/SNP/snp (Year: 2015).*
DbSNP Submitted SNP(ss) Report in Submission Format for NCBI Assay Id(ss#): ss1712236750, Mar. 4, 2015, 1 printed page from https://www.ncbi.nlm.nih.gov/projects/SNP/snp (Year: 2015).*
Hanson, E.K. et al "A Y-short tandem repeat specific DNA enhancement strategy to aid the analysis of late reported (56 days) sexual assault cases" Medicine, Science and the Law 2014, vol. 54(4) 209-218 (Year: 2014).*
Mills, R.E. "An initial map of insertion and deletion (INDEL) variation in the human genome" Genome Research 16(9):1182-90 • Oct. (Year: 2006).*
Submitted SNP(ss) Report in Submission Format ss1378755170, Aug 16, 2014, pp. 1-2 printed from www.ncbi.nlm.nih.gov. (Year: 2014).*
Ayers et al. "Distint conformers of transmissible misfolded SOD1 distinguish human SOD1-FALS from other forms of familial and sporadic ALS" Acta Neuropathol, 132:827-840 (2016).
Chi et al. "Distinct neurological disorders with C9orf72 mutations: genetics, pathogenesis, and therapy" Neuroscience & Biobehavioral Reviews, 66:127-142 (2016).
Deloach et al. "A retrospective review of the progress in amyotrophic lateral sclerosis drug discovery over the last decade and a look at the latest strategies" Expert Opin. Drug Discov., 10(10):1099-1118 (2015).

(Continued)

*Primary Examiner* — Stephen T Kapushoc
(74) *Attorney, Agent, or Firm* — Myers Bigel, P.A (57) ABSTRACT

Provided herein according to some embodiments is a method for detecting a short tandem repeat (STR) variant in the SOD1, TARDBP or C9orf72 gene region comprising measuring the length of the STR variant. In some embodiments, the method V includes obtaining a biological sample containing genomic DNA from a subject, optionally isolating the genomic DNA from the sample. Also provided is a method for determining a diagnosis or a prognosis for a neurodegenerative disease, including: measuring a length of a short tandem repeat (STR) variant in the SOD1, TARDBP or C9orf72 gene region, and determining the diagnosis or prognosis based upon the length. Further provided is a method of treatment for a neurodegenerative disease including: administering a therapeutic agent to a subject based upon a length of a short tandem repeat (STR) variant in the SOD1, TARDBP or C9orf72 gene region in the subject. Also provided is a kit for detecting a (STR) variant in the SOD1, TARDBP or C9orf72 gene region.

5 Claims, 3 Drawing Sheets
Specification includes a Sequence Listing.

(56) References Cited

OTHER PUBLICATIONS

Extended European Search Report corresponding to EP17811055, dated Nov. 27, 2019 (14 pp).
Gatto et al. "Intrafamilial variable phenotype including corticobasal syndrome in a family with p.P201L mutation in the MAPT gene: first report in South America" Neurobiology of Aging, 53:195.e11-195.e17 (2017).
Herdewyn et al. "Whole-genome sequencing reveals a coding non-pathogenic variant tagging a non-coding pathogenic hexanucleotide repeat expansion in C0orf72 as cause of amyotrophic lateral sclerosis" Human Molecular Genetics, 21(11):2412-2419 (2012).
Ittner et al. "FTD and ALS—Translating mouse studies into clinical trials" Nat. Rev. Neurol., 11:360-366 (2015).
Martinez et al. "Drugs in clinical development for the treatment of amyotrophic lateral sclerosis" Expert Opinion on Investigational Drugs, 26(4):403-414 (2017).
McAllum et al. "Therapeutic effects of CuII(atsm) in the SOD1-G37R mouse model of amyotrophic lateral sclerosis" Amyotrophic Lateral Sclerosis and Frontotemporal Degeneration, 14:586-590 (2013).
Onesto et al. "Gene-specific mitochondria dysfunctions in human TARDBP and C9ORF72 fibroblasts" Acta Neuropathologica Communications, 4(1) (14 pp) (2014).
Xi et al. "Jump from Pre-mutation to Pathological Expansion in C9orf72" The American Journal of Human Genertics, 96:962-970 (2015).
Written Opinion and International Search Report corresponding to International Patent Application No. PCT/US17/36682, dated Sep. 5, 2017, 11 pages.
Gijselinck et al., "A C9orf72 Promoter Repeat Expansion in a Flanders-Belgian Cohort With Disorders of the Frontotemporal Lobar Degeneration-Amyotrophic Lateral Sclerosis Spectrum: A Gene Identification Study", The Lancet Neurology, 11(1):54-65 (2012).
Anderson et al. "Phenotypic heterogeneity in motor neuron disease patients with CuZn-superoxide dismutase mutations in Scandinavia" Brain, 120:1723-1737 (1997).
Chio et al. "Phenotypic heterogeneity of amyotrophic lateral sclerosis: a population based study" J Neurol Neurosurg Psychiatry, 82(7):740-746 (2011).
Gymrek et al. "Genome-Wide Analysis of Expression Short Tandem Repeats" Abstract at the 2014 meeting of the American Society of Human Genetics.
Highley et al. "Loss of nuclear TDP-43 in amyotrophic lateral sclerosis (ALS) causes altered expression of splicing machinery and widespread dysregulation of RNA splicing in motor neurones" Neuropathology and Applied Neurobiology, 40:670-685 (2014).
Imamura et al. "The Src/c-Abl pathway is a potential therapeutic target in amyotrophic lateral sclerosis" Sci. Transl. Med., 9:391 (2017).
Laird et al. "Family-based designs in the age of large-scale gene-association studies" Nat Rev Genet, 7(5):385-394 (2006) (Abstract only).
Linneretz et al. "The cis-regulatory effect of an Alzheimer's disease-associated poly-T locus on expression of TOMM40 and apolipoprotein E genes" Alzheimers Dement,. 10(5):541-551 (2014).
Roses et al. "African-American TOMM40'523-APOE haplotypes are admixture of West African and Caucasian alleles" Alzheimer's & Dementia, pp. 1-10 (2014).
Roses et al. "Structural variants can be more informative for disease diagnostics, prognostics and translation than current SNP mapping and exon sequencing" Expert Opinion of Drug Metabolism & Toxicology, 12(2):135-147 (2016).
Rubinsztein et al. "Autophagy modulation as a potential therapeutic target for diverse diseases" Nat. Rev. Drug Discov., 11(9):709-730 (2012).
Saeed et al. "Age and founder effect of SOD1 A4V mutation causing ALS" Neurology, 72:1634-1639 (2009).
Sanger et al. "DNA sequencing with chain-terminating inhibitors" Proc. Natl. Acad. Sci. U.S.A,. 74(12):5463-5467 (1977).
Williams et al. "Copper delivery to the CNS by CuATSM effectively treats motor neuron disease in SOD(G93A) mice co-expressing the Copper-Chaperone-for-SOD" Neurobiol Dis., 89:1-9 (2016).
Willems et al. "The landscape of human STR variation" Genome Research, 24:1894-1904 (2014).

* cited by examiner

SEQUENCE LISTING

```
<160> NUMBER OF SEQ ID NOS: 11

<210> SEQ ID NO 1
<211> LENGTH: 64
<212> TYPE: DNA
<213> ORGANISM: Homo sapiens

<400> SEQUENCE: 1
tttcaccgtt accttgtctt aaattaaaaa aaaaaaaaat agagagcact tctaattacg     60
attt                                                                 64

<210> SEQ ID NO 2
<211> LENGTH: 65
<212> TYPE: DNA
<213> ORGANISM: Homo sapiens

<400> SEQUENCE: 2
tttcaccgtt accttgtctt aaattaaaaa aaaaaaaaaa tagagagcac ttctaattac     60
gattt                                                                65

<210> SEQ ID NO 3
<211> LENGTH: 66
<212> TYPE: DNA
<213> ORGANISM: Homo sapiens

<400> SEQUENCE: 3
tttcaccgtt accttgtctt aaattaaaaa aaaaaaaaaa atagagagca cttctaatta     60
cgattt                                                               66

<210> SEQ ID NO 4
<211> LENGTH: 67
<212> TYPE: DNA
<213> ORGANISM: Homo sapiens

<400> SEQUENCE: 4
tttcaccgtt accttgtctt aaattaaaaa aaaaaaaaaa aatagagagc acttctaatt     60
acgattt                                                              67

<210> SEQ ID NO 5
<211> LENGTH: 68
<212> TYPE: DNA
<213> ORGANISM: Homo sapiens

<400> SEQUENCE: 5
```

```
tttcaccgtt accttgtctt aaattaaaaa aaaaaaaaaa aaatagagag cacttctaat    60
tacgattt                                                              68

<210> SEQ ID NO 6
<211> LENGTH: 25
<212> TYPE: DNA
<213> ORGANISM: Artificial
<220> FEATURE:
<223> OTHER INFORMATION: PCR Primer

<400> SEQUENCE: 6
atcaaaagta ttacatatga aagtg                                           25

<210> SEQ ID NO 7
<211> LENGTH: 17
<212> TYPE: DNA
<213> ORGANISM: Artificial
<220> FEATURE:
<223> OTHER INFORMATION: PCR Primer

<400> SEQUENCE: 7
tgtagagctt gaggtgt                                                    17

<210> SEQ ID NO 8
<211> LENGTH: 487
<212> TYPE: DNA
<213> ORGANISM: Artificial
<220> FEATURE:
<223> OTHER INFORMATION: 487 bp amplicon

<400> SEQUENCE: 8
atcaaaagta ttacatatga aagtgagaat aactacataa aatgtctatt ttcatcaaat    60
aagtctaatt tagactccaa tacagtatta acagctcaaa ctttgacggt gaacaatcct   120
tttccacctt aatgcagtgt aggaagaata gcacacatta aagtttgtta cgaaaataga   180
gtttattaaa aacatcccta ttgttttgag gagctttcac cgttaccttg tcttaaatta   240
aaaaaaaaaa aaaaaataga gagcacttct aattacgatt tgtaaacttt ttaaagtcaa   300
aacttttaaa aagttacagc aaaaagggta atatttattc atattttcag tattttttgt   360
tattttgtgg ctatttttaa atagaaggga agcaatcaaa ttgcttacag ttccccacca   420
gctggcgcgg ggctgcagta cagcgggagc ggatataata cagcatctgt acacctcaag   480
ctctaca                                                             487

<210> SEQ ID NO 9
<211> LENGTH: 25
<212> TYPE: DNA
<213> ORGANISM: Artificial
<220> FEATURE:
<223> OTHER INFORMATION: PCR Primer

<400> SEQUENCE: 9
tgagaataac tacataaaat gtcta                                           25

<210> SEQ ID NO 10
<211> LENGTH: 22
<212> TYPE: DNA
<213> ORGANISM: Artificial
<220> FEATURE:
<223> OTHER INFORMATION: PCR Primer

<400> SEQUENCE: 10
tgtacagatg ctgtattata tc                                              22
```

```
<210> SEQ ID NO 11
<211> LENGTH: 450
<212> TYPE: DNA
<213> ORGANISM: Artificial
<220> FEATURE:
<223> OTHER INFORMATION: 450 bp amplicon

<400> SEQUENCE: 11
tgagaataac tacataaaat gtctattttc atcaaataag tctaatttag actccaatac      60
agtattaaca gctcaaactt tgacggtgaa caatccttt ccaccttaat gcagtgtagg     120
aagaatagca cacattaaag tttgttacga aaatagagtt tattaaaaac atccctattg     180
ttttgaggag ctttcaccgt taccttgtct taaattaaaa aaaaaaaaaa aaatagagag     240
cacttctaat tacgatttgt aaacttttta aagtcaaaac tttttaaaaag ttacagcaaa    300 aagggtaata tttattcata ttttcagtat tttttgttat tttgtggcta tttttaaata    360
gaagggaagc aatcaaattg cttacagttc cccaccagct ggcgcgggc tgcagtacag     420 cgggagcgga tataatacag catctgtaca                                     450
```

METHODS FOR DETECTING STRUCTURAL VARIANTS IN NEURODEGENERATIVE DISEASE

BACKGROUND

Amyotrophic lateral sclerosis (ALS) is a progressive neurodegenerative disease in which motor neurons controlling voluntary movements are adversely affected. In some cases, the disease is associated with inherited genetic mutations (familial ALS or fALS). In other cases in which there is no family history of the disease and it presents as an isolated case, the disease is considered to be sporadic (sALS). However, genetic disposition may be involved in sALS cases.

On a genetic level, ALS is a complex disease with a great deal of inter-individual and intra-familial phenotypic variability. See, e.g., Chio et al. (2011) *J Neurol Neurosurg Psychiatry* 82(7):740-746; Andersen et al. (1997) *Brain* 120:1723-1737. There are multiple uncommon single nucleotide polymorphisms (SNPs) assigned as specific "mutations" for each of several ALS genes. More than 150 separate SNP variants within the gene encoding Cu/Zn superoxide dismutase (SOD1) have been proposed as associated with ALS to date.

SUMMARY

Provided herein according to some embodiments is a method for detecting a short tandem repeat (STR) variant in the SOD1, TARDBP or C9orf72 gene region comprising measuring the length of the STR variant. In some embodiments, the method includes obtaining a biological sample containing genomic DNA from a subject, optionally isolating the genomic DNA from the sample.

Also provided is a method for determining a diagnosis for a neurodegenerative disease, including: measuring a length of a short tandem repeat (STR) variant in the SOD1, TARDBP or C9ort72 gene region, and determining the diagnosis based upon the length.

Further provided is a method for determining a prognosis for a neurodegenerative disease, including: measuring a length of a short tandem repeat (STR) variant in the SOD1, TARDBP or C9orf72 gene region, and determining the prognosis based upon the length.

Still further provided is a method of treatment for a neurodegenerative disease including: administering a therapeutic agent to a subject based upon a length of a short tandem repeat (STR) variant in the SOD1, TARDBP or C9ort72 gene region.

Also provided is the use or preparation of a medicament or therapeutic agent as taught herein for the treatment of a neurodegenerative disease in a subject based upon a length of a short tandem repeat (STR) variant in the SOD1, TARDBP or C9orf72 gene region.

Further provided is a method of stratifying a subject in a clinical trial for treatment of a neurodegenerative disease comprising: administering the treatment to a subject based upon a length of a short tandem repeat (STR) variant in the SOD1, TARDBP or C9orf72 gene region.

Still further provided is an in vitro stem cell and/or transgenic animal (e.g., a non-human primate (e.g., lemur such as mouse or dwarf lemur), or a rodent such as rat or mouse)) model of neurodegenerative diseases, wherein the cells of said model comprise a short tandem repeat (STR) variant as taught herein.

Also provided is a kit for detecting a (STR) variant in the SOD1, TARDBP or C9orf72 gene region, comprising at least one reagent that specifically detects the STR variant. In some embodiments, the kit is for detecting the variant in a subject having or suspected to have ALS.

In some embodiments of any of the above methods, use, model or kit, the STR variant includes a simple sequence repeat (SSR) of at least 8, 9, 10, 11, 12, 13 or 14 consecutive bases.

In some embodiments of any of the above methods, use, model or kit, the STR includes at least three, four or five length variants.

In some embodiments of any of the above methods, use, model or kit, the STR variant is a poly-T or a poly-A SSR variant.

In some embodiments of any of the above methods, use, model or kit, the measuring includes Sanger DNA sequencing, a size-based assay (e.g., gel or capillary electrophoresis), or both.

In some embodiments of any of the above methods, use or model, the measuring comprises nested PCR.

In some embodiments of any of the above methods, use, model or kit, the STR variant is a poly-T or poly-A SSR variant between the SOD1 gene and the SCAF4 gene in chromosome 21 (position chr21:33,043,422-33,043,440 of the Genome Reference Consortium Human Genome Assembly Release GRCh37.p13). In some embodiments, the variant has 14, 15, 16, 17 or 18 poly-T or poly-A residues. In some embodiments, the variant has 14, 15 or 16 poly-T or poly-A residues. In some embodiments, the variant has 17 or 18 poly-T or poly-A residues. In some embodiments, the variant has 18 poly-T or poly-A residues.

In some embodiments of any of the above methods, use, model or kit, the method includes genotyping by measuring the length of the STR variant at each allele (phased or unphased).

In some embodiments of any of the above methods, use, model or kit, a poly-T or poly-A length of 18 indicates a diagnosis and/or more rapid progression of the neurodegenerative disease.

In some embodiments of any of the above methods, use, model or kit, the subject carries a SOD1 mutation and/or a fALS-C9orf72 mutation.

BRIEF DESCRIPTION OF THE DRAWINGS

FIG. 5 presents a contingency analysis of the relationship by T18 Carriage Mosaic Plot. This plot shows the proportional distribution of individuals affected with ALS compared to controls stratified by carriage of at least one T18 SV1 allele. The two columns in the plot reflect either carriage of at least one SV1 T18 allele (T18) or no carriage of a T18 allele (N). The key at the right side of the plot shows the coding for affected with ALS (shaded) versus control (no shading). The height of the shaded block in each column corresponds to the proportion of the stratified sample affected with ALS. The scale of the y-axis (far left) shows the proportions for the disease stratification with the entire subset of individuals in each SV1 length category corresponding to 1. The width of each column is proportional to the number of individuals in the two T18 carriage classifications.

DETAILED DESCRIPTION OF EMBODIMENTS

The present invention is explained in greater detail below. This description is not intended to be a detailed catalog of all the different ways in which the invention may be implemented, or all of the features that may be added. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

As used in the description of the invention and the appended claims, the singular forms "a", "an" and "the" are intended to include the plural forms as well, unless the context clearly indicates otherwise. Also, as used herein, "and/or" refers to and encompasses any and all possible combinations of one or more of the listed items, as well as the lack of combinations when interpreted in the alternative ("or").

Included in the disclosures herein is an SSR found to be highly associated with a quantitative phenotype of ALS, and replicated using 32 of the more than 150 proposed SNP mutations for SOD1 in ALS. In addition, this SSR also identified other cases of ALS previously not localized to the SOD1 region that were classified as so-called sporadic disease. Furthermore, several ALS cases classified at other familial ALS locations on the genome were also identified in non-SOD1 disease controls (Normal Controls 3/459; sporadic 3/32, C9ORF72 2/1, and TARDBP 1/15). This suggests that the SSR may be present in additional genetic disease loci in a greater frequency than normal controls and may indicate that the 18T is a common factor at other ALS gene regions, or that additional similar SSRs may be in other disease loci regions. This is also supported by finding similar frequencies in cases without a known gene at the time of patient selection—so-called "sporadic."

SSRs have been postulated to affect gene expression, both quantitative amount and alternative splicing, which is involved in human disease. See, e.g., Smith et al. 2000 *TIBS* 25:381-388; Caceres et al. 2002 *TRENDS in Genetics* 18(4): 186-193. Involved in this process is a localized organelle called the spliceosome.

Thus, and without wishing to be bound by theory, the SSR may implicate the spliceosome for involvement in the pathogenesis mechanism for ALS by its cis-localized location in the SOD1 gene region. The spliceosome is the functional local micro-organelle to direct alternative splicing of transcripts across the genome. These constituent factors are found throughout the genome and expressed in a finely-coordinated and finely-structured organelle that splice out introns that are located in transcribed pre-mRNA and control the reattachment of selected exon sequences, resulting in alternatively spliced forms of the structural gene. Aberrant splicing of mRNA or decreased products of functional species can result from SSR sequences that are within introns of the gene or nearby in cis-regulatory regions of the chromosomal strand.

This suggests that control elements may alter the structure and/or amount of functional mRNA and affect necessary functions and interactions of the gene.

Highley et al. (2014 *Neuropathology and Applied Neurobiology* 40:670-685) reported with respect to TDP-43, a transcriptional repressor/splicing factor encoded by TAR-DBP and associated with forms of motor neuron disease at the TDP-43 locus, that a loss of nuclear TDP-43 function was associated with RNA processing abnormalities in ALS motor neurons in a small number of ALS-TDP-43 patients' autopsied microdissected neuronal tissue. Thus, they found that key functional pathways affected included those central to RNA metabolism.

As reported in the data presented herein, it was found that other patients characterized with another disease gene-associated loci, different from SOD1, carry the uncommon SOD1 T18 variant at SV1, suggesting a multi-locus combination affecting gene splicing and contributing to disease progression.

In fact, it may be that many of the numerous known genetic mutations associated with ALS (e.g., SOD SNPs) may be on the backbone of an STR variant as taught herein.

The biological activity of the SOD gene may be affected by the STR in the SOD1 gene region. For example, inheritance of particular STR variants may differentially affect SOD expression (e.g., expression level and/or differential splicing).

Functional effects of structural variants is not without precedent. The age of onset of Alzheimer's disease has been shown to be dependent on TOMM40 '523-APOE cis-haplotypes, which are length difference variations of an informative STR located within a highly associated region of the genome, with varying cis-haplotypes across ethnic groups including, but not limited to, Caucasians, African-Americans, West Africans, and Japanese according to allele frequency studies. Additionally, the variants effect expression levels of both genes. See, e.g., Linnertz et al. (2014) *Alzheimers Dement.* 10(5):541-551.

As taught herein, it has been found that a particular STR in the SOD gene region is associated with a form of ALS associated with the shortest duration until death of an ALS patient.

"Structural variants" or "SV" are all genomic insertions, deletions, inversion and microsatellites. There are currently over 7 million SVs in the human genome, with more than 1 million associated with a long simple sequence repeat (SSR) or short tandem repeat (STR) (Roses et al., Expert Opinion of Drug Metabolism & Toxicology 2016).

A "short tandem repeat" or "STR" as used herein is a place in the genome where one base, or a short stretch of bases (e.g., 2, 3, 4, 5 or 6 consecutive bases) are repeated in tandem. A particular form of a polymorphic STR, e.g., a particular length, is a "variant" thereof.

As used herein, a "simple sequence repeat" or "SSR" is a form of STR in which there is one repeated (consecutive) base (i.e., A, T, C or G in genomic DNA). Examples of known polymorphic SSRs include, for example, the poly-T variant SSR at human locus rs10524523 (TOMM40 '523).

The biological effects of SSRs, and more generally STRs, are understudied. Many STRs existing in the genome have never been identified because, in the rush to sequence the whole genome rapidly and less expensively, the field has turned to next generation sequencing (NGS). But, unfortunately, currently available NGS methods do not identify more than 8-10 nucleotides accurately for assay purposes, thus missing differentiation of larger polymorphic length STRs.

"Polymorphism" as used herein refers to the existence of two or more different nucleotide sequences at a particular locus in the DNA of the genome. Polymorphisms can serve as genetic markers and may also be referred to as genetic variants. Polymorphisms include nucleotide substitutions, insertions, deletions and microsatellites, e.g., STRs, and may in some instances result in detectable differences in gene expression or protein function. A polymorphic site is a nucleotide position within a locus at which the nucleotide sequence varies from a reference sequence in at least one individual in a population.

"Haplotype" as used herein refers to a genetic variant or combination of variants carried on at least one chromosome in an individual. A cis-haplotype in some embodiments includes multiple polymorphic loci on the same copy of a chromosome or haploid DNA molecule. Absent evidence to the contrary, a cis-haplotype is presumed to represent a combination of multiple loci that are likely to be transmitted together during meiosis. Each human carries a pair of haplotypes for any given genetic locus, consisting of sequences inherited on the homologous chromosomes from two parents. These haplotypes may be identical or may represent two different genetic variants for the given locus. Haplotyping is a process for determining one or more haplotypes in an individual. Haplotype determination may include use of family pedigrees, molecular techniques and/or statistical inference.

A "variant" or "genetic variant" as used herein, refers to a specific isoform of a haplotype found in a population, the specific form differing from other forms of the same haplotype in the sequence of at least one, and frequently more than one, variant sites or nucleotides within the sequence of the gene. "Variants" include isoforms having single nucleotide polymorphisms (SNPs) and STRs. Reference to the presence of a variant means a particular variant, i.e., particular nucleotides or STR pattern/length at particular polymorphic sites, rather than just the presence of any variance in the gene locus.

"Isoform" as used herein means a particular form of a gene, mRNA, cDNA or the protein encoded thereby, distinguished from other forms by its particular sequence and/or structure. For example, the ApoE 4 isoform of apolipoprotein E as opposed to the ApoE2 or ApoE 3 isoforms.

The term "genotype" in the context of this invention refers to the particular allelic form of a gene, which can be defined by the particular nucleotide(s) present in a nucleic acid sequence at a particular site(s). Genotype may also indicate the pair of alleles present at one or more polymorphic loci. For diploid organisms, such as humans, two haplotypes make up a genotype. Genotyping is any process for determining a genotype of an individual, e.g., by nucleic acid amplification, antibody binding, or other chemical analysis. The resulting genotype may in some embodiments be unphased, meaning that the sequences found are not known to be derived from one parental chromosome or the other.

"Linkage disequilibrium" as used herein means the non-random association of alleles at two or more loci. Linkage disequilibrium describes a situation in which some combinations of alleles or genetic markers occur more or less frequently in a population than would be expected from a random formation of haplotypes from alleles based on their frequencies. Non-random associations between polymorphisms at different loci are measured by the degree of linkage disequilibrium.

A "subject" according to some embodiments is an individual whose genotype(s) or haplotype(s) are or have been determined, and may have been recorded in conjunction with the individual's condition (i.e., disease or disorder status, including, but not limited to, the disease risk status, age of onset prediction, progression prognosis, etc.).

Subjects are preferably, but not limited to, human subjects. The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric, but in some embodiments adult or geriatric subjects are preferred. In some embodiments, subjects are at least 20,30, or 40 years of age. Subjects may also include animal subjects, particularly mammalian subjects such as canines, felines, bovines, caprines, equines, ovines, porcines, rodents (e.g., rats and mice), lagomorphs, primates (including non-human primates such as mouse or dwarf lemurs), etc., screened for veterinary medicine or pharmaceutical drug development purposes.

In some embodiments, the subject has or is suspected to have ALS. In some embodiments, the subject has one or more SOD1 mutations, including, but not limited to, the A4V mutation and/or @100K mutation. In some embodiments, the subject has a C9orf72 mutation. See Saeed et al. (2009) *Neurology* 72:1634-1639.

"Treat," "treating," or "treatment" as used herein refers to any type of measure that imparts a benefit to a subject afflicted with or at risk for developing a disease, including improvement in the condition of the subject (e.g., in one or more symptoms), delay in the onset or progression of the disease, etc. Treatment may include any drug, procedure, lifestyle change, or other adjustment introduced in attempt to effect a change in a particular aspect of a subject's health (i.e., directed to a particular disease, disorder, or condition). In some embodiments as taught herein, treatment is for a neurodegenerative disease such as amyotrophic lateral sclerosis (ALS), Alzheimer's Disease (AD), Lewy Body dementia (LBD), frontotemporal dementia (FTD), etc.

"Biological sample" as used herein refers to a material containing a nucleic acid or protein of interest. Biological samples containing DNA include hair, skin, cheek swab, and biological fluids such as blood, serum, plasma, sputum, lymphatic fluid, semen, vaginal mucus, feces, urine, spinal fluid, and the like. Isolation of nucleic acid from such samples is well known to those skilled in the art.

"Gene" as used herein means a segment of DNA that contains all the information for the regulated biosynthesis of an RNA product, including promoters, exons, introns, and other untranslated regions that may control expression.

"Genetic locus" or "locus" as used herein means a location on a chromosome or DNA molecule, often corresponding to a gene region or a physical or phenotypic feature or to a particular nucleotide or stretch of nucleotides. Loci is the plural form of locus.

As noted, disclosed herein is a genetic locus in the SOD1 gene region between the SOD1 gene and the SCAF4 gene in chromosome 21 (at position chr21:33,043,422-33,043, 440 of the Genome Reference Consortium Human Genome Assembly Release GRCh37.p13) that shows strong association with an aggressive form of ALS. This multi-allelic microsatellite, which is referred to as "SV1" in the data herein, is currently unnamed in the public databases. Variants of 14A, 15A, 16A, 17A, and 18A were present in the genotyping cohort reported herein.

A variant named rs71714698 in the gene SCAF4 (just downstream from SOD1) was previously listed in an older version (build 138) of dbSNP, with a variation described as an "AA" insertion (if combined with flanking As, this would be 17A or 19A). In more recent builds of dbSNP, rs71714698 is no longer listed. There is currently a single-base "A" insertion named rs573116164 in the region. If combined with flanking As, it would be 17A or 18A. Due to these inconsistencies in description in the public databases, the variable poly-A or poly-T at position chr21:33,043,422-33,043, 440 of the Genome Reference Consortium Human Genome Assembly Release GRCh37.p13 described herein (which also includes 14A, 15A and 16A as variants) is termed SV1.

Figure 1:
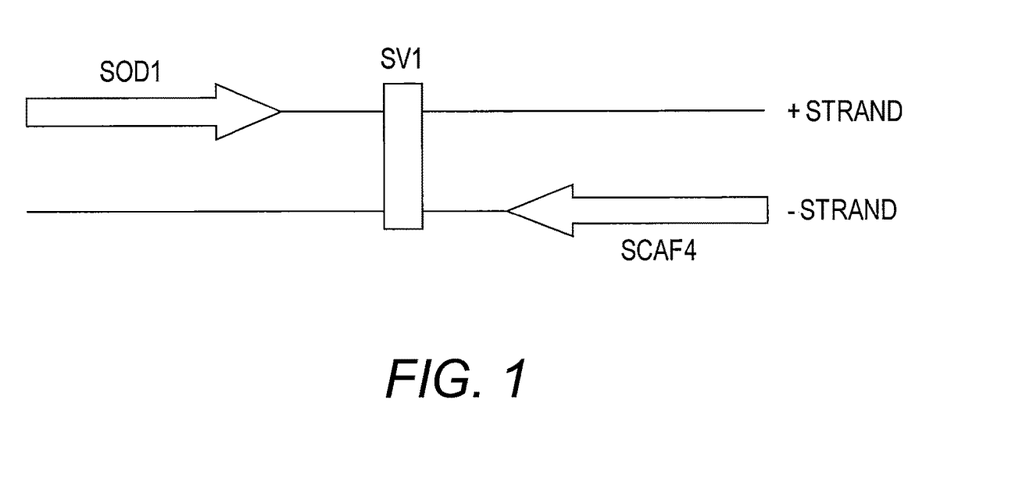
FIG. 1 presents a diagram of the relative location of SV1 in the SOD1 region on Chromosome 21. SV1 is downstream (3') of the SOD1 gene, and also downstream (3') of another gene, SCAF4, which is encoded on the other (minus) strand of the Chromosome 21. On the plus strand where SOD1 is encoded, SV1 is a poly-A; on the minus strand where SCAF4 is encoded, SV1 is its compliment, i.e., a poly-T.

Analysis of SV1 reveals that it is downstream (3') of the SOD1 gene, and also downstream (3') of another gene, SCAF4, which is encoded on the other (minus) strand of the chromosome, as illustrated in FIG. 1. On the plus strand where SOD1 is encoded, SV1 is a poly-A; on the minus strand where SCAF4 is encoded, SV1 is its compliment, i.e., a poly-T.

Interestingly, SV1 is flanked on both sides with binding sites for the transcription factor polymerase (RNA) II subunit A (POLR2A). POLR2A is the largest subunit of RNA polymerase II, and responsible for synthesizing messenger RNA in eukaryotes.

"Cu/Zn superoxide dismutase", "superoxide dismutase", "SOD" and "SOD1" are used herein interchangeably to refer to an enzyme encoded by the SOD1 gene in humans, or to the gene itself (depending on context), located on chromosome 21. One of three human superoxide dismutases, SOD1 has been implicated in apoptosis and amyotrophic lateral sclerosis.

"SCAF4" or "SR-Related CTD-Associated Factor 4" located on the minus strand of chromosome 21 encodes a member of the arginine/serine-rich splicing factor family involved in transcription and/or pre-mRNA splicing. Thus, aberrant splicing may be involved on multiple levels due to structural variants in this region due to possible effects on expression of SCAF4.

"Associated with" as used herein means the occurrence together of two or more characteristics more often than would be expected by chance alone. An example of association involves a feature on the surface of white blood cells called HLA (HLA stands for human leukocyte antigen). A particular HLA type, HLA type B-27, is associated with an increased risk for a number of diseases including ankylosing spondylitis. Ankylosing spondylitis is 87 times more likely to occur in people with HLA B-27 than in the general population.

"Drug" as used herein refers to a chemical entity or biological product, or combination of chemical entities or biological products, administered to a person to treat, including prevent, delay the onset or control (e.g., delay the progression), of a disease or condition. The term "drug" as used herein is synonymous with the terms "medicine," "medicament," "therapeutic intervention," or "pharmaceutical product." In some embodiments, the drug may be approved by a government agency for treatment of at least one specific disease or condition.

While not wishing to be bound by theory, STRs or SSRs found in non-coding regions of genes may exert their functional effects directly, or tag or otherwise be in linkage disequilibrium with causal variants, which may, e.g., modulate the expression of genes involved in a disease or condition. For example, the effects may occur through alternative splicing of the subsequent exon or through modulation of expression level, with such altered gene expression determining disease state, susceptibility, course, and/or drug efficacy or likelihood of adverse events.

Supporting this, a genome-wide analysis of expression with multi-allelic STR or SSR genotypes reported significant associations of STR variations and expression profiles, explaining on average about 22% of the cis-heritability of the expression levels of the genes after controlling for nearby SNPs. Gymrek et al., Genome-Wide Analysis of Expression Short Tandem Repeats, Abstract at the 2014 meeting of the American Society of Human Genetics. See also Willems et al., The landscape of human STR variation, Genome Research 24:1894-1904 (2014).

Determining the length of a STR or SSR variant in a SOD gene region as taught herein may be combined with other genetic and/or medical history determinations to reach a prognosis of disease course.

Measuring the Length of a STR Variant

Measuring the length of a STR or SSR as taught herein may be carried out by direct sequencing of the genomic DNA region of interest, with an oligonucleotide probe labeled with a suitable detectable group, and/or by means of an amplification reaction such as a polymerase chain reaction or ligase chain reaction (the product of which amplification reaction may then be detected with a labeled oligonucleotide probe or a number of other techniques, including sequencing).

In some embodiments, the measuring is carried out in vitro after obtaining a biological sample having genomic DNA from a subject. In some embodiments, the genomic DNA is isolated from the sample.

Sequencing methods include, for example, dideoxynucleotide chain termination techniques, such as those described by Sanger et al. (1977) Proc. Natl. Acad. Sci. U.S.A. 74(12), 5463-5467. As noted above, current "next-generation" sequencing may not be able to accurately measure an STR/SSR longer than 8-10 nucleotides in length.

It will be appreciated that determining the length of a genomic STR/SSR, for example a poly-T or a poly-A stretch, may be complicated by the "stuttering" of DNA polymerase in, for example, sequencing reactions utilizing PCR techniques. See, e.g., Fazekas et al. (2010) *BioTechniques* 48:277-285. This stuttering of the DNA polymerase can result in the generation of PCR products of various lengths, which may reduce the quality of the sequence data after a mononucleotide repeat of 10 or more bases, often to the point where the sequence data becomes difficult to interpret or even unreadable.

In some embodiments, the methods include the use of nested pcr, in which a second set of primers is used to amplify a region within the region amplified by a first set of primers, thereby increasing accuracy/specificity.

Detection can also be performed by making use of assays that detect the relative length of the relevant portion of genomic DNA (e.g., by gel filtration, gel electrophoresis, capillary electrophoresis, etc. of an amplified portion of the region).

In some embodiments, the methods may include longrange PCR and/or DNA cloning into plasmids.

In some embodiments, the methods may include at least two methods (e.g., 2 or 3 methods) to determine the length of an STR variant.

In some embodiments, the methods may include genotyping by measuring the length of the STR variant at each allele (phased or unphased).

For example, genotyping of, analysis of the length of, and/or sequencing of STR variants may be performed as described in Roses et al. *Alzheimer's & Dementia* (2014) 1-10, in which nested PCR and Sanger sequencing were performed in duplicate (method 1), and PCR product size was determined using electrophoresis, and comparison with results of subcloned DNA fragments with a known number of residues (method 2).

Further, the detecting step may include the step of detecting whether the subject is heterozygous or homozygous at the loci of interest.

Some embodiments of the present invention may include steps implemented by a computer and/or computer program products, including analog and/or digital hardware, and/or computer program instructions. These computer program instructions may be provided to a processor of a general purpose computer, special purpose computer, Application Specific Integrated Circuits (ASIC), and/or other programmable data processing apparatus, such that the instructions, which execute via the processor of the computer and/or other programmable data processing apparatus, create means for implementing the functions/acts specified. Other software, such as an operating system, also may be included. It will be further appreciated that the functionality of the sequencing module, genotyping module, multiple sequence alignment module, mapping module and/or other modules described herein may be embodied, at least in part, using discrete hardware components, one or more ASIC and/or one or more special purpose digital processors and/or computers.

It will be appreciated that the use of a computer and/or computer program products may be used in conjunction with sequencing protocols to analyze and refine sequencing data obtained from such protocols. In some embodiments, electropherograms obtained using Sanger sequencing techniques may be further refined and analyzed using such computer and/or computer program products. For example, commercially available computer software products for genetic analysis running on a computer, such as, but not limited to, SEQUENCHER® (Gene Codes Corp., Ann Arbor Mich.), GeneMarker® (SoftGenetics, LLC, State College, Pa.) DNASTAR® (DNASTAR, Inc. Madison, Wis.) and the like, as well as other proprietary software packages used by sequencing vendors, may be used to assist in the analysis of and determination of the precise length of an STR or SSR, for example, a poly-T or poly-A tract, within a region of DNA sequence.

Targeted Therapy

Genetic variants as described herein may be used in practical application to determine the course of treatment of a subject afflicted with or at increased risk of developing a condition (e.g., a neurodegenerative disease and/or a condition associated with one or more variants of SOD). This may include, e.g., determining which active agent and/or course of treatment and/or dosage to administer and/or timing of treatment based upon the presence or absence of the genetic variant or variants and/or proceeding to administer an appropriate treatment based thereon.

The genetic variant or variants as described herein may also be used to establish or confirm a diagnosis of a particular disease or condition (e.g., a neurodegenerative disease such as ALS) in order to determine the need for treatment and the appropriate course of intervention.

The genetic variant or variants as described herein may also be used for stratifying/enrichment in a clinical trial to investigate the efficacy of new treatments for a specific patient population.

Riluzole is a medication approved for treatment of ALS in the United States by the Food and Drug Administration. It slows the progression of ALS, thought to be by reducing levels of glutamate in the brain. Riluzole can cause significant side effects, though, such as dizziness, gastrointestinal conditions and changes in liver function. However, upon determining a more aggressive form of ALS by detecting the length of a poly-T or poly-A variant in the SOD1 gene region, it may be desirable to proceed with treatment with riluzole or another neuronal excitability modulating agent.

Other known neuronal excitability modulating agents include, but are not limited to, NMDA antagonists such as remacemide (investigated for treatment of Huntington's disease), mematine (used to treat dementia and Alzheimer's disease), and budipine; and anti-seizure drugs such as lamotrigine, gabapentin and retigabine. See also US 2015/0190363 to Woolf et al.

Other therapies for ALS may include administration of copper-based agents such as copper-ATSM (copper chelated with diacetylbis(4-methyl-thiosemicarbazone)). See Williams et al., Neurobiol Dis. 2016 May;89:1-9.

Edaravone (3-methyl-1-phenyl-2-pyrazolin-5-one) is also an approved medication in the United States for treatment of ALS. Edaravone is a member of the substituted 2-pyrazolin-5-one class of free radical scavengers. Though one of the few approved options for treatment of ALS, edaravone is an expensive intravenous infusion and can cause significant side effects, such as hives, swelling, and shortness of breath. However, upon determining a more aggressive form of ALS by detecting the length of a poly-T or poly-A variant in the SOD1 gene region, it may be desirable to proceed with treatment with edaravone.

Still other agents that may be use for treatment of neurodegenerative disease such as ALS include tyrosine kinase inhibitors, such as inhibitors of the tyrosine kinases Src and c-Abl. See Imamura et al., Sci. Transl. Med. 2017 May 24; 9:391. Examples include, but are not limited to, bosutinib, masitinib, nilotinib, etc.

Without wishing to be bound by theory, it is thought that inhibition of Src and c-Abl may stimulate autophagy. Thus, other agents that boost autophagy may also be used for treatment of ALS. Examples of agents that boost autophagy include, but are not limited to, rapamycin, L-NAME (N-L-arginine methyl ester), imidazoline receptor agonists such as clonidine and rilmenidine, etc. See Rubinsztein et al., Nat. Rev. Drug Discov. 2012 September; 11(9):709-730.

Models of Neurodegenerative Disease

STR variants as taught herein may be provided in in vitro stem cell models and/or transgenic animal (e.g., a non-human primate such as a mouse or dwarf lemur, or a rodent such as rat or mouse) models of neurodegenerative diseases such as ALS, which are useful for, e.g., research and/or drug screening and development purposes. See, e.g., US 2014/0322237 to Eggan et al.; US 2010/0028931 to Eggan et al.; US 2002/0062493 to Eggan et al., which are incorporated by reference herein.

The present invention is described in more detail in the following non-limiting examples.

EXAMPLES

To discover genetic structural variants (SVs) that are linked to ALS phenotypic differences, both familial ALS (fALS) and sporadic ALS (sALS) cases were incorporated into a discovery case-control study. Forty-four families were included, which allowed both assessment of allele transmission and variant length variability compared to phenotypes such as age of onset and duration, not only between individual cases, but also within families. See Laird et al. (2006) *Nat Rev Genet* 7(5):385-394.

There is increasing evidence that the genetics in the regions surrounding SOD1 is a tightly-linked disease modifying factor that affects the mode of inheritance as well as phenotype for various ALS SOD1 mutations such as A4V. See Saeed et al. (2009) *Neurology* 72:1634-1639. Once identified, these factors could shed light on the pathogenic mechanism for ALS and be used to guide decisions for treatment or drug development.

Structural variants were selected in and surrounding the SOD1, TARBDP and C9ORF72 gene regions (Table 1) and investigated in an ALS case-control cohort consisting of 811 subjects in total. The cohort included 234 ALS cases: 200 fALS cases (171 SOD1, 19 TARDBP and 10 C9ORF72 patients), 34 sALS; and 577 age-matched controls not known to have any neurodegenerative disease at the time of their assessment.

Known mutations associated with ALS were also investigated in this study, including 32 SOD1 mutations distributed across the gene. Of the 32 mutations, the A4V mutation (n=28) and G100K mutation (n=1) were found with the 18T allele of SV1, as discussed below.

Inclusion of sALS mutation negative patients allows preliminary examination of broader involvement of structural variants in ALS beyond SOD1 mutation positive cases. To explore the possibility that SVs in candidate ALS genes may be associated with ALS and related phenotypes, 9 TARBDP, 5 SOD1 and 3 C9ORF72 SVs were investigated (Table 1). These candidate genes were selected based on prior evidence that disease causing mutations may be underpinned by structural variants, and underlying pathology may suggest evidence of protein/RNA abnormal regulation. Structural variants within the genes had high impact scores based on our scoring algorithm dbSV.

Figure 2:
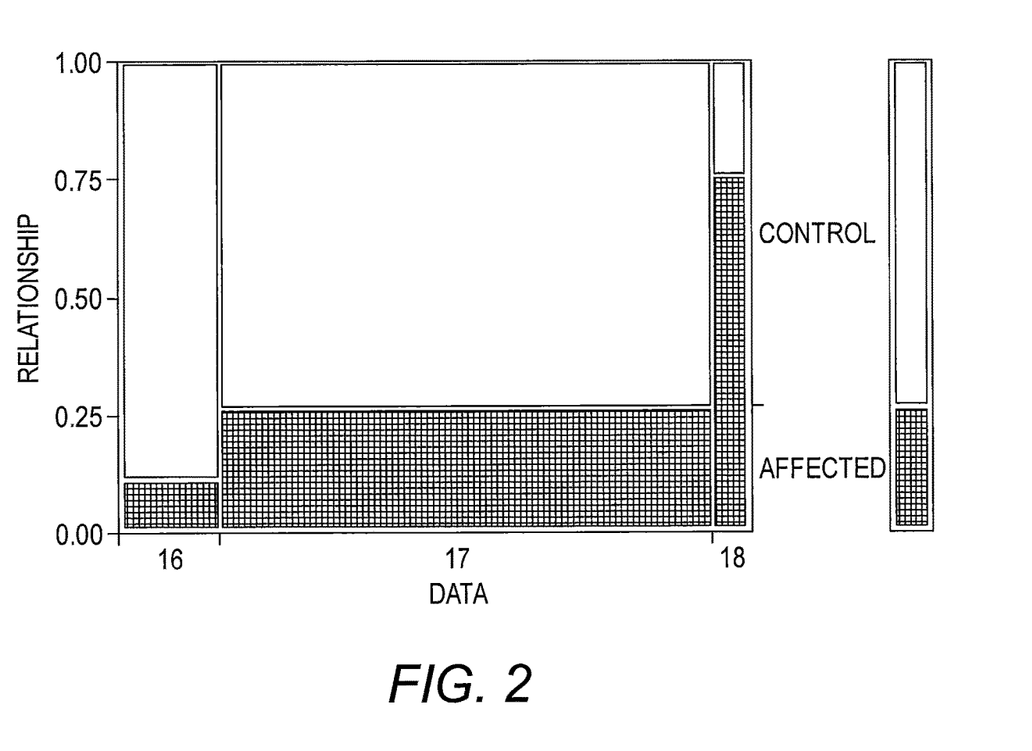
FIG. 2 provides a histogram illustrating poly T variability of SV1 amongst ALS cases vs. controls. Alleles represented in each histogram16T: 22 case, controls 174; 17T 251 case, control 713; 1 8T 55 case, 18 control; The histogram above shows the distribution of alleles for SV1 amongst cases and controls, the 18T allele in significantly enriched for ALS cases in particular for the A4V ALS cases.

Demographics (n=number of subjects in each category); cases and controls are represented as raw values (total 803: cases 234, controls 569). Average age of cases and controls 49.1 years (SD 12.6), controls 49.3 (SD 12.6); age of onset of cases 48.6 (SD 12.6). Duration 47.4 months (SD 54.4), unknown (n=8), still living (n=14). Gender 385 female, 418 male. Ethnicity, Caucasian n=742, Asian n=6, African American n=54. Structural variant SV1 18T allele was associated with a greater number of ALS cases than controls. The population of ALS patients who carried at least one 18T allele included: 29 SOD1 cases (28 A4V, 1 G100K), 3 sALS cases, 1 TARDBP N325B case and 2 C9ORF72 fALS cases compared to controls (p=1*10$^{-12}$, Likelihood ratio test, Table 2). In particular, the association appears to be driven by the SV1 18T allele (FIG. 2).

TABLE 1

Structural variation investigated in ALS eases and Controls

| SEARCH NAME | CHROM. NO. | CHROMOSOME POSITION | VARIANT TYPE | SYMBOL | ASSOCIATED GENE |
|---|---|---|---|---|---|
| rs34839760 | 1 | 11,071,714 | SSR | 19A | TARDBP |
| rs36071114 | 1 | 11,072,477 | insertion | —/G | TARDBP |
| rs144319432 | 1 | 11,072,533 | deletion | —/C | TARDBP |
|  | 1 | 11,084,334 | SSR | 11T | TARDBP |
| rs145446787 | 1 | 11,085,001 | insertion | —/GTTTT | TARDBP |
| rs5772439 | 1 | 11,085,004 | insertion | —/TGTTT | TARDBP |
| rs3059695 | 1 | 11,085,005 | mixed | —/GTTTT/TGTTT | TARDBP |
| rs113627607 | 1 | 11,095,586 | SSR | 9ATC | TARDBP |
| rs576496603 | 1 | 11,102,454 | SSR | 11TGGA | TARDBP |
|  | 21 | 33,028,704 | SSR | 13A | SOD1 |
| rs36232192 | 21 | 33,030,349 | deletion | 50bp | SOD1 |
| rs1041740 | 21 | 33,040,162 | SNP | C/T | SOD1 |
| rs35497195 | 21 | 33,040,164 | insertion | —/C | SOD1 |
| SV1 | 21 | 33,043,422 | SSR | 17A | SOD1 |
| rs143561967 | 9 | 27,573,522 | deletion | —/GCCCG | C9orf72 |
| rs34524354 | 9 | 27,549,775 | SSR | 16A | C9orf72 |
| rs35184194 | 9 | 27,555,557 | SSR | 19T | C9orf72 |
| rs71492752 | 9 | 27,564,155 | SSR | 23A | C9orf72 |

TABLE 2

Structural variants in a case/control study for ALS with p-values <0.05

| VARIANT | Map number | STATISTIC | DF | VALUE | PROB |
|---|---|---|---|---|---|
| SV1 | 33043422 | Likelihood Ratio Chi-Square | 3 | 60.3974 | <.0001 |
| rs36232192 | 33030349 | Likelihood Ratio Chi-Square | 1 | 10.2014 | 0.0014 |
| rs36233090 | 33030275 | Likelihood Ratio Chi-Square | 1 | 7.5147 | 0.0061 |
| rs34839760 | 11011656 | Likelihood Ratio Chi-Square | 4 | 13.6353 | 0.0086 |
| rs17881732 | 33040157 | Likelihood Ratio Chi-Square | 1 | 4.2988 | 0.0381 |
| rs61443822 | 11017220 | Likelihood Ratio Chi-Square | 5 | 11.7577 | 0.0383 |

Examination of the ALS patients who carry the SV1 18T allele reveals that of the 31 ALS cases who carry this allele, 27 are positive for the A4V mutation. The 27 A4V ALS patients are from 17 families. In order to determine if the association between SV1 and ALS holds when taking into account family structures, generalized estimating equations were used to model the probability that individuals with specific SV1 alleles would be affected. The model takes into account the correlation structure induced by the design of using individuals from families affected by ALS as cases and unrelated individuals as controls. The analysis showed an association (p=0.02) between SV1 and ALS-SOD1.

Examination of the A4V and G100K ALS missense mutations reveals that they are 11327 bp and 3790 kb upstream from SV1, respectively. Examination of Caucasian Linkage disequilibrium (LD) of the SOD1 region where A4V and G100K reside and SV1 suggests a modest LD, but it is possible that in ALS the SOD1 gene region is in higher LD due to possible thunder effects. See Saeed et al. (2009) *Neurology* 72:1634-1639.

Figure 3:
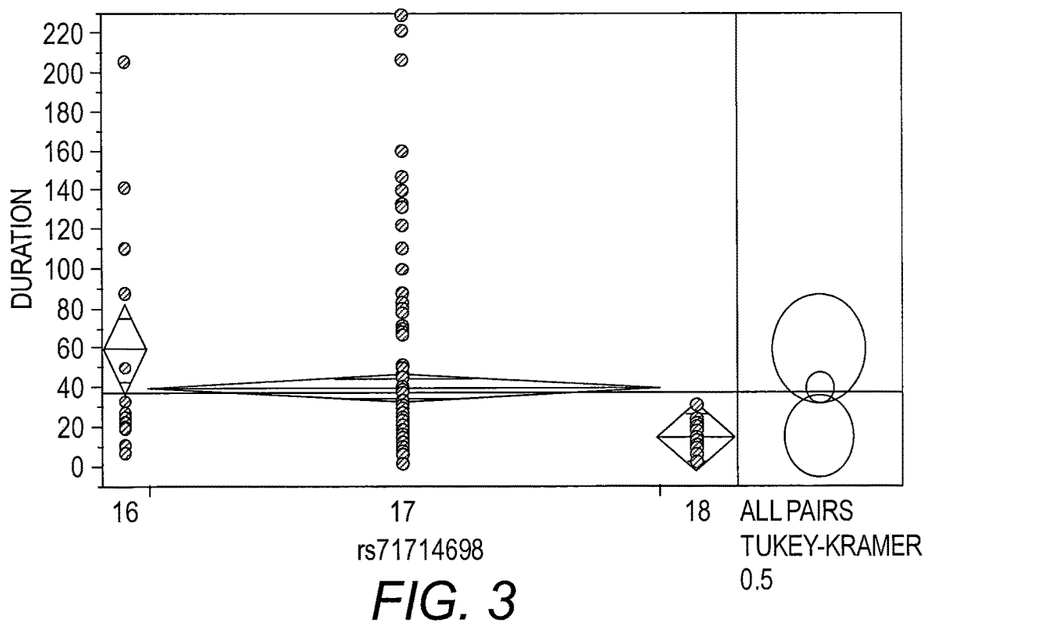
FIG. 3 presents a graph of a one-way analysis of duration in months by SV1 allele length. The pattern of longer length being associated with a worse outcome is confirmed by these data. Mean duration decreases with increasing allele length. One caution is that the group sizes are different. This result is for Caucasians, FALS-SOD1 diagnosis.
Figure 4:
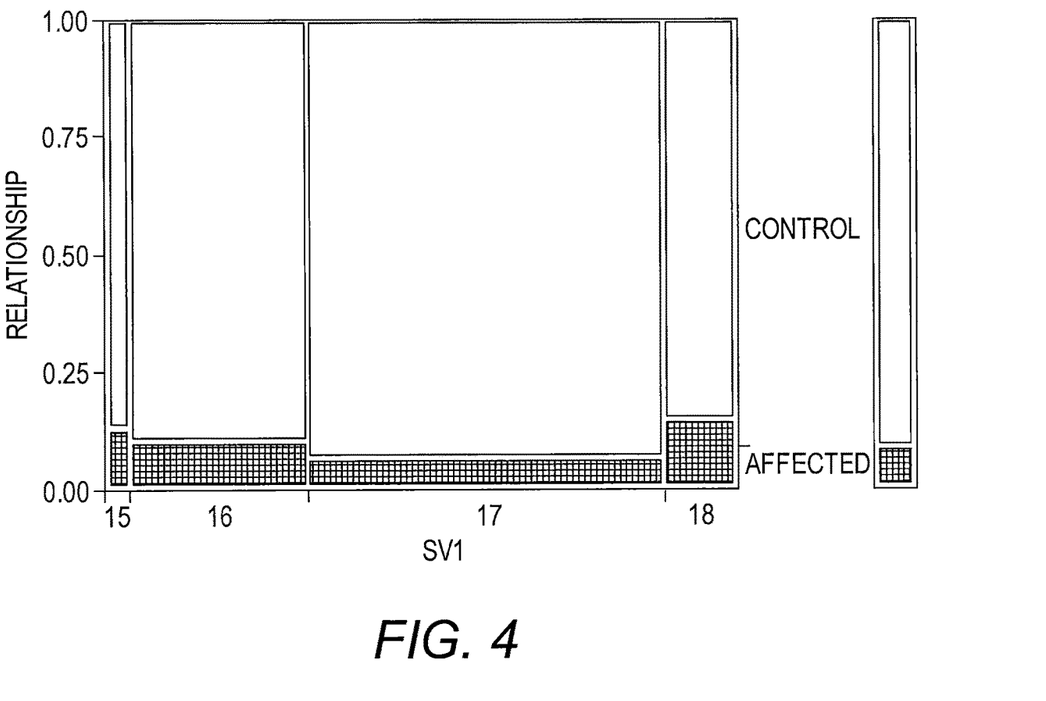
FIG. 4 presents a histogram illustrating diagnosis of fALS-SOD compared to control. This plot shows the proportional distribution of individuals affected with ALS compared to controls stratified by SV1 allele length. The four columns in the plot represent SV1 allele length classifications. The key at the right side of the plot shows the coding for affected with ALS (shaded) versus control (no shading). The height of the shaded block in each column corresponds to the proportion of the stratified sample affected with ALS. The scale of the y-axis (far left) shows the proportions for the disease stratification with the entire subset of individuals in each SV1 length category corresponding to 1. The width of each column is proportional to the number of individuals in the four SV1 allele length classifications.
Figure 5:
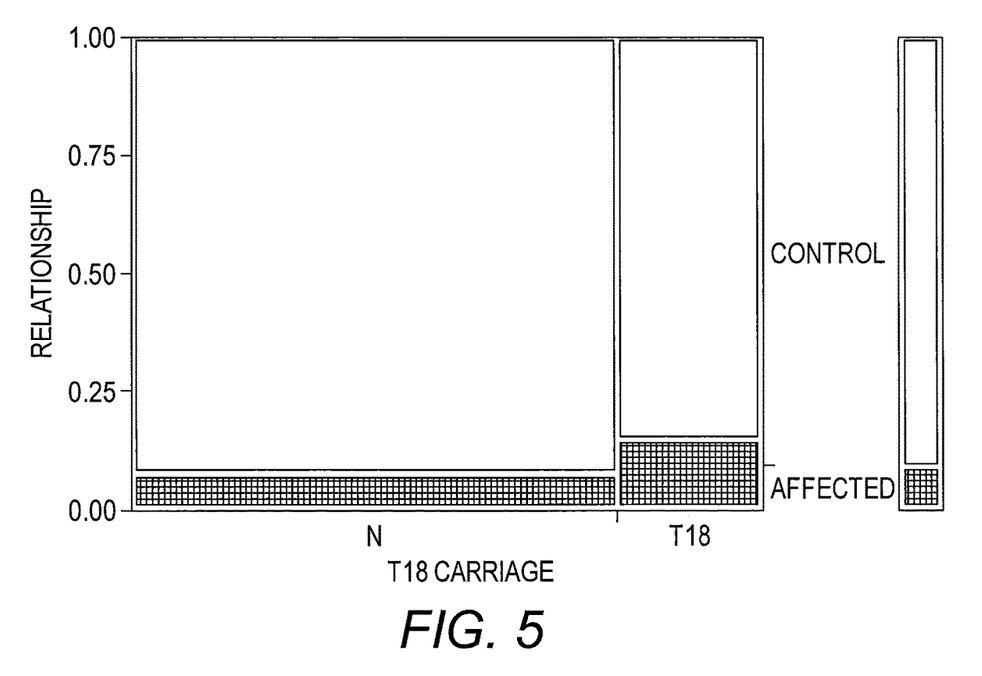

Duration and age of onset was then examined for SV1 in ALS cases, and it was found that the 18T SV1 variant was associated with the shortest duration until death of the patient when compared to the 17T or 16T variant (FIG. 3, p-value 0.0054). A4V patients when split into two groups: 18T (27), or not 18T (36 patients) had an average age of onset in years for 18T of 53.15 (SD 8.4) and not 18T of 48.6 (SD 12.5); for duration in months 18T 38.62 (SD 5.8) and not 18T 13.72 (SD 7). SV1 associations with ALS and specifically duration will be tested at completion of the validation experiment.

In silico analysis of SV1 reveals that it is flanked on both sides with binding sites for the transcription factor POLR2A. POLR2A is the largest subunit of RNA polymerase II, and responsible for synthesizing messenger RNA in eukaryotes. The varying length of SV1 may affect transcription of genes in the region, including SOD1. This observation supports the evidence of an ALS risk modifying factor raised in other studies such as that by Saeed et al. 2009.

Of the 526 controls that returned genotyping data for SV1:

2 controls had a genotype of 14A, 16A
13 controls had a genotype of 16A, 16A
2 controls had a genotype of 15A, 17A
142 controls had a genotype of 16A, 17A
346 controls had a genotype of 17A, 17A
21 controls had a genotype of 17A, 18A In the ALS cases were 16A, 17A and 18A lengths. Specifically, of the 158 ALS patients that returned genotyping for SV1:

13 patients had a genotype of 16A, 17A
92 patients had a genotype of 17A,17A
50 patients had a genotype of 17A, 18A
3 had a genotype of 18A, 18A Structural variant rs36232192 is a 50 bp deletion polymorphism in the SOD1 promoter, 1684 bp upstream of the ATG, and has been previously associated with an increased age of symptom onset in various populations of ALS patients. Broom et al. (2008) *Amyotroph Lateral Scler* 9(4):229-237. A recent study observed a similar trend with the 50 bp deletion in homozygous sALS subjects. Milani et al. (2012) *J Neural Sci* 313(1-2):75-78.

In the present study, a delay of onset based on the 50 bp deletion was not observed. However, the present study is predominantly composed of fALS subjects, compared to the two prior studies predominantly composed of sALS subjects. The functional consequence of the 50 bp deletion has been reported to be a reduction of SOD1 expression in vitro, and this may also be relevant to fALS. Overall in this case-control study we observed a p-value of 0.0014, with proportionally fewer cases displaying the 50 bp deletion compared to controls. Preliminary examination of age of onset for this polymorphism between subjects who carry at least one deletion returned a value 47.8 years (SD 11.4), and those that are homozygous for the 50 bp insertion is 48.9 years of age (SD 12.9). Survival for those patients who carry a 50 bp deletion was 54.5 months (1 deletion) (SD 53) and 45.5 months (no deletions) (SD 54.9). Three subjects who were homozygous for the 50 bp deletion had onset ages of 72, 41 and 39. Disease durations for these three patients were 11, 14 months, and still living, respectively.

Other structural variants were also tested. Those having a p-value of 0.1 or less calculated with likelihood ratio chi-square statistic overall ALS compared to control are presented in Table 3. SV1 had an overall p-value of $5*10^{-13}$.

TABLE 3

ALS SV Analysis Results

| Variant | P-value |
|---|---|
| SV1 | <.0001 |
| rs36232192 | 0.0014 |
| rs36233090 | 0.0061 |
| rs34839760 | 0.0086 |
| rs17881732 | 0.0381 |
| rs61443822 | 0.0383 |
| chr1: 11,084,334 | 0.0604 |
| rs113888039 | 0.0677 |
| chr21: 33,037,001 (SNP, G) | 0.0707 |

Detection of Variant Length at SV1

The sequence of the 14A SV1 variant with +/−25 bp flanking is:

(SEQ ID NO: 1)
TTTCACCGTTACCTTGTCTTAAATT[AAAAAAAAAAAAAA]TAGAGAGCA

CTTCTAATTACGATTT

The sequence of the 15A SV1 variant with +/−25 bp flanking is:

(SEQ ID NO: 2)
TTTCACCGTTACCTTGTCTTAAATT[AAAAAAAAAAAAAAA]TAGAGAGC

ACTTCTAATTACGATTT

The sequence of the 16A SV1 variant with +/−25 bp flanking is:

(SEQ ID NO: 3)
TTTCACCGTTACCTTGTCTTAAATT[AAAAAAAAAAAAAAAA]TAGAGAG

CACTTCTAATTACGATTT

The sequence of the 17A SV1 variant with +/−25 bp flanking is:

(SEQ ID NO: 4)
TTTCACCGTTACCTTGTCTTAAATT[AAAAAAAAAAAAAAAAA]TAGAGA

GCACTTCTAATTACGATTT

The sequence of the 18A SV1 variant with +/−25 bp flanking is:

(SEQ ID NO: 5)
TTTCACCGTTACCTTGTCTTAAATT[AAAAAAAAAAAAAAAAAA]TAGAG

AGCACTTCTAATTACGATTT

The SV1 region was analyzed using 2-step PCR amplification. The primers for the first step were:

```
Forward primer step 1:
                             (SEQ ID NO: 6)
ATCAAAAGTATTACATATGAAAGTG
Reverse primer step 1:
                             (SEQ ID NO: 7)
TGTAGAGCTTGAGGTGT
```

Using the 17A SV1 variant as an example, this produced a 487 bp amplicon with the sequence (SEQ ID NO:8):

ATCAAAAGTATTACATATGAAAGTGAGAATAACTACATAAAATGTCTAT

TTTCATCAAATAAGTCTAATTTAGACTCCAATACAGTATTAACAGCTCA

AACTTTGACGGTGAACAATCCTTTTCCACCTTAATGCAGTGTAGGAAGA

ATAGCACACATTAAAGTTTGTTACGAAAATAGAGTTTATTAAAAACATC

CCTATTGTTTTGAGGAGCTTTCACCGTTACCTTGTCTTAAATTAAAAAA

AAAAAAAAAAATAGAGAGCACTTCTAATTACGATTTGTAAACTTTTTAA

AGTCAAAACTTTTAAAAAGTTACAGCAAAAGGGTAATATTTATTCATA

TTTTCAGTATTTTTTGTTATTTTGTGGCTATTTTAAATAGAAGGGAAG

CAATCAAATTGCTTACAGTTCCCCACCAGCTGGCGCGGGCTGCAGTAC

AGCGGGAGCGGATATAATACAGCATCTGTACACCTCAAGCTCTACA

This product was then PCR-amplified with a second set of primers:

```
Forward primer step 2:
                             (SEQ ID NO: 9)
TGAGAATAACTACATAAAATGTCTA
Reverse primer step 2:
                             (SEQ ID NO: 10)
TGTACAGATGCTGTATTATATC
```

Using the 17A SV1 variant as an example, this produced a 450 bp amplicon with sequence (SEQ ID NO:11):

TGAGAATAACTACATAAAATGTCTATTTTCATCAAATAAGTCTAATTTA

GACTCCAATACAGTATTAACAGCTCAAACTTTGACGGTGAACAATCCTT

TTCCACCTTAATGCAGTGTAGGAAGAATAGCACACATTAAAGTTTGTTA

CGAAAATAGAGTTTATTAAAAACATCCCTATTGTTTTGAGGAGCTTTCA

CCGTTACCTTGTCTTAAATTAAAAAAAAAAAAAAAAATAGAGAGCACTT

CTAATTACGATTTGTAAACTTTTTAAAGTCAAAACTTTTAAAAAGTTAC

AGCAAAAGGGTAATATTTATTCATATTTTCAGTATTTTTGTTATTTT

GTGGCTATTTTAAATAGAAGGGAAGCAATCAAATTGCTTACAGTTCCC

CACCAGCTGGCGCGGGCTGCAGTACAGCGGGAGCGGATATAATACAGC

ATCTGTACA

This amplicon was sequenced using Sanger sequencing, using the "Reverse primer step 2" as the sequencing primer.

Electropherograms resulting from this analysis were further refined by software analysis (Polymorphic DNA Technologies, Inc., Alameda, Calif.).

SV1 Data Replication

The association of the SV1 variant with ALS phenotypes was further investigated in an additional cohort of novel cases of both familial (fALS) and sporadic (sALS) cases in a case-control study. Thirty-seven families were included in this sample set, which allowed assessment of allele transmission and variation of SV1 to a number of ALS phenotypes including age of onset and duration between unrelated cases and within families.

Demographics (n=number of subjects in each category): total 828: cases 207, controls 621. Average age of cases was 52.1 years (SD 14.9), and controls 51.2 years (SD 14.7); Duration 50.3 months (SD 51.7), unknown (n=8), still living (n=8). Gender: 407 female, 420 male (1 missing gender). Ethnicity: Caucasian n=823, Hispanic/white=1, Other=3.

Age of Onset fALS-C9orf72-54 subjects—57.4 years of age (yoa) (SD 11.3)

fALS-FUS—33 subjects—40.0 yoa (SD 16.5)

fALS-SOD1-60 subjects—50.5 yoa (SD 11.8)

sALS 60 subjects—56.05 yoa (SD 15.5)

Association Between SV1 and ALS

Overall, there is a statistically significant (p=0.0296, Likelihood Ratio test) association observed between carriage of the T18 allele of SV1 and fALS-SOD1 in comparison to controls. There is also a statistically significant (p=0.01, Likelihood Ratio test) association observed between carriage of the T17 or T18 allele of SV1 and fALS-C9orf72 in comparison to controls. Comparing genotypes that contain T18 with genotypes that do not contain T18 gives a highly statistically significant difference between fALS-SOD1 and control, p=0.017 (Likelihood ratio test).

Considering SV1 genotypes, T18 carriage vs. no T18 carriage, the odds ratio comparing fALS-SOD1 with control determined in this study is 2.2 (95% CI 1.2-4.3).

Note that there are about 10× as many controls as individuals in each diagnostic category. For the fALS-SOD1 individuals, the duration of the disease is shorter for carriers of T18 compared to the other allele lengths; however, the difference is not statistically significant (data not shown).

Generalized estimating equations were used to determine if the association between SV1 and ALS holds when taking into account family structures. This approach takes into account the correlation structure induced by the design of using individuals from families affected by ALS as cases and unrelated individuals as controls. The analysis showed a statistically-significant association of (p=0.03) between SV1 and fALS-SOD1.

TABLE 4

Contingency Table
SV1 By Relationship

| | Count<br>Total %<br>Col %<br>Row % | | |
|---|---|---|---|
| | affected | control | Total |
| 15 | 5<br>0.48<br>5.56<br>12.82 | 34<br>3.24<br>3.55<br>87.18 | 39<br>3.72 |
| 16 | 29<br>2.77<br>32.22<br>9.86 | 265<br>25.29<br>27.66<br>90.14 | 294<br>28.05 |
| 17 | 39<br>3.72<br>43.33<br>6.54 | 557<br>53.15<br>58.14<br>93.46 | 596<br>56.87 |
| 18 | 17<br>1.62<br>18.89<br>14.29 | 102<br>9.73<br>10.65<br>85.71 | 119<br>11.35 |
| Total | 90<br>8.59 | 958<br>91.41 | 1048 |

TABLE 5

Tests

| N | DF | −LogLike | RSquare (U) |
|---|---|---|---|
| 1048 | 3 | 4.4870267 | 0.0146 |

| Test | ChiSquare | Prob > ChiSq |
|---|---|---|
| Likelihood Ratio | 8.974 | 0.0296* |
| Pearson | 9.594 | 0.0224* |

TABLE 6 fALS-SOD1 and Control

| SV1_1 | SV1_2 | N Rows | N(control) | N(FALS-SOD1) |
|---|---|---|---|---|
| Missing | | 157 | 142 | 15 |
| 15 | 15 | 5 | 5 | 0 |
| 15 | 16 | 8 | 8 | 0 |
| 15 | 17 | 20 | 16 | 4 |

TABLE 6-continued fALS-SOD1 and Control

| SV1_1 | SV1_2 | N Rows | N(control) | N(FALS-SOD1) |
|---|---|---|---|---|
| 15 | 18 | 1 | 0 | 1 |
| 16 | 16 | 3 | 3 | 0 |
| 16 | 17 | 188 | 173 | 15 |
| 16 | 18 | 92 | 78 | 14 |
| 17 | 17 | 181 | 172 | 9 |
| 17 | 18 | 26 | 24 | 2 | fALS-SOD1

Comparison of individuals with SV1 genotypes carrying T18 with individuals with SV1 genotypes that do not carry T18. Comparison is between fALS-SOD1 cases and controls, p=0.017 (Likelihood ratio test).

TABLE 7

Contingency Table
T18 Carriage By Relationship

| | Count<br>Total %<br>Col %<br>Row % | | |
|---|---|---|---|
| | affected | control | Total |
| N | 28<br>5.34<br>62.22<br>6.91 | 377<br>71.95<br>78.71<br>93.09 | 405<br>77.29 |
| T18 | 17<br>3.24<br>37.78<br>14.29 | 102<br>19.47<br>21.29<br>85.71 | 119<br>22.71 |
| Total | 45<br>8.59 | 479<br>91.41 | 524 |

TABLE 8

Tests

| N | DF | −LogLike | RSquare (U) |
|---|---|---|---|
| 524 | 1 | 2.8573023 | 0.0186 |

| Test | ChiSquare | Prob > ChiSq |
|---|---|---|
| Likelihood Ratio | 5.715 | 0.0168* |
| Pearson | 6.368 | 0.0116* |

| Fisher's Exact Test | Prob | Alternative Hypothesis |
|---|---|---|
| Left | 0.0124* | Prob(Relationship = control) is greater for T18 Carriage = N than T18 |
| Right | 0.9951 | Prob(Relationship = control) is greater for T18 Carriage = T18 than N |

TABLE 8-continued

| Tests | | |
|---|---|---|
| 2-Tail | 0.0155* | Prob(Relationship = control) is different across T18 Carriage |

TABLE 9

Genotype data, comparing specific diagnosis with control
(p value, likelihood ratio test) for T18 carriage

| T18 carriage | p value |
|---|---|
| fALS-SOD1 | 0.017 |
| C9orf72 | 0.85 |

TABLE 9-continued

Genotype data, comparing specific diagnosis with control
(p value, likelihood ratio test) for T18 carriage

| T18 carriage | p value |
|---|---|
| fALS-FUS | 0.73 |
| sALS | 0.88 |

The foregoing is illustrative of the present invention, and is not to be construed as limiting thereof. The invention is defined by the following claims, with equivalents of the claims to be included therein.

That which is claimed is:

1. A method for detecting a simple sequence repeat (SSR) variant of a subject, said method comprising:
    obtaining a biological sample from the subject, said sample comprising genomic DNA,
    isolating said genomic DNA from said sample, and
    measuring the length of the SSR variant, wherein the SSR variant of the subject is 14, 15, or 18 poly-T or poly-A residues at SV1, and
    wherein said measuring comprises Sanger DNA sequencing, a size-based assay, or both.

2. The method of claim 1, wherein said measuring comprises nested PCR.

3. The method of claim 1, wherein said method comprises genotyping by measuring the length of the SSR variant at each allele (phased or unphased).

4. The method of claim 1, wherein the SV1 variant of the subject has a poly-T or poly-A length of 18.

5. The method of claim 1, wherein said measuring comprises gel or capillary electrophoresis.

* * * * *

UNITED STATES PATENT AND TRADEMARK OFFICE
CERTIFICATE OF CORRECTION

PATENT NO. : 11,001,893 B2
APPLICATION NO. : 16/308315
DATED : May 11, 2021
INVENTOR(S) : Allen D. Roses It is certified that error appears in the above-identified patent and that said Letters Patent is hereby corrected as shown below:

On the Title Page (71) Applicants: Please remove "Ann M. Saunders"

(56) References Cited, OTHER PUBLICATIONS, Column 2, Line 7: Please correct "SBP(ss)" to read -- SNP(ss) --

(57) ABSTRACT, Line 5: Please correct "method V includes" to read -- method includes --

In the Specification

Column 1, Line 40: Please correct "C9ort72" to read -- C9orf72 --

Column 1, Line 51: Please correct "C9ort72" to read -- C9orf72 --

Column 2, Line 58: Please correct "1 8T" to read -- 18T --

Column 3, Line 65: Please correct "Controls 3/459" to read -- Controls - 3/459 --

Column 9, Line 10: Please correct "per" to read -- pcr --

Column 12, Line 33: Please insert a paragraph break between "n=54." and "Structural"

Signed and Sealed this
Seventh Day of September, 2021

Drew Hirshfeld
*Performing the Functions and Duties of the
Under Secretary of Commerce for Intellectual Property and
Director of the United States Patent and Trademark Office*